(12) United States Patent
Vivier

(10) Patent No.: US 12,396,965 B2
(45) Date of Patent: Aug. 26, 2025

(54) PUTRESCINE TOPICAL BARRIER FORMULATION

(71) Applicant: VIVIER CANADA INC., Vaudreuil-Dorion (CA)

(72) Inventor: Ghislain Vivier, St-Lazare (CA)

(73) Assignee: VIVIER CANADA INC., Vaudreuil-Dorion (CA)

( * ) Notice: Subject to any disclaimer, the term of this patent is extended or adjusted under 35 U.S.C. 154(b) by 0 days.

(21) Appl. No.: 18/659,232

(22) Filed: May 9, 2024

(65) Prior Publication Data

US 2024/0293340 A1    Sep. 5, 2024

Related U.S. Application Data

(63) Continuation of application No. 17/302,527, filed on May 5, 2021, now abandoned, which is a continuation of application No. 16/883,864, filed on May 26, 2020, now abandoned, which is a continuation of application No. 16/349,030, filed as application No. PCT/CA2018/050008 on Jan. 5, 2018, now abandoned.

(60) Provisional application No. 62/443,158, filed on Jan. 6, 2017.

(51) Int. Cl.

| | | |
|---|---|---|
| *A61K 31/132* | (2006.01) | |
| *A61K 8/31* | (2006.01) | |
| *A61K 8/34* | (2006.01) | |
| *A61K 8/40* | (2006.01) | |
| *A61K 8/41* | (2006.01) | |
| *A61K 8/46* | (2006.01) | |
| *A61K 8/55* | (2006.01) | |
| *A61K 8/67* | (2006.01) | |
| *A61K 8/92* | (2006.01) | |
| *A61K 9/00* | (2006.01) | |
| *A61K 9/06* | (2006.01) | |
| *A61K 31/205* | (2006.01) | |
| *A61K 47/10* | (2017.01) | |
| *A61K 47/44* | (2017.01) | |
| *A61P 17/00* | (2006.01) | |
| *A61P 17/02* | (2006.01) | |

(52) U.S. Cl.
CPC .......... *A61K 31/132* (2013.01); *A61K 9/0014* (2013.01); *A61K 31/205* (2013.01); *A61K 47/44* (2013.01); *A61P 17/02* (2018.01)

(58) Field of Classification Search
None
See application file for complete search history.

(56) References Cited

U.S. PATENT DOCUMENTS

| | | |
|---|---|---|
| 5,885,982 A | 3/1999 | Dolynchuk et al. |
| 2020/0281872 A1 | 9/2020 | Vivier |

FOREIGN PATENT DOCUMENTS

| | | |
|---|---|---|
| CA | 2706630 A1 | 6/2009 |
| EP | 2604254 B1 | 12/2016 |
| WO | 9951213 A2 | 10/1999 |
| WO | 2006048671 A1 | 5/2006 |
| WO | 2012175686 A2 | 12/2012 |

OTHER PUBLICATIONS

Dolynchuk et al., Effect of putrescine on tissue transglutaminase activity in wounds: decreased breaking strength and increased matrix fucoprotein solubility, plastic and reconstructive surgery, 1994, pp. 567-573, vol. 93.
Dolynchuk, Inhibition of tissue transglutaminase and e (gamma-glutamyl) lysine cross-linking in human hypertrophic scar, Wound Repair and Regeneration, 1996, pp. 16-20, vol. 4.
Dolynchuk et al., Topical putrescine (Fibrostat) in treatment of hypertrophic scars: phase II study, Plastic and Reconstructive Surgery, 1996, p. 117-23; discussion p. 124-5, vol. 97.
International Searching Authority, International search report and written opinion, Mar. 21, 2018, pp. 1-13, Canada.
Jeong et al., Resurfacing of pitted facial acne scars with a long-pulsed er: YAG Laser, The American Society for Dermatologic Sergery Inc., Feb. 2001, pp. 107-110.
Lynde, Moisturizers: What they are and how they work, Skin Therapy Letter, Dec. 2001, https://www.skintherapyletter.com/eczema/how-moisturizers-work/, vol. 6 No. 13.
MacKay et al., Nutritional Support for Wound Healing, Alternative Medicine Review, 2003, pp. 359-377, vol. 8 No. 4.
Rowe et al., Handbook of Pharmaceutical Excipients sixth edition, The Pharmaceutical Press and American Pharmacists Association, 2009, 917 pages.
Traikovitch, Use of Topical Ascorbic Acid and Its Effects on Photodamaged Skin Topography, Arch Otolaryngol head neck Surg., Oct. 1999, pp. 1091-1098, vol. 125.
Vivier, V-STAT Advanced Scar Gel (30 ml), Vivier Pharma Inc., May 24, 2017, https://www.vivierpharma.com/en_US/V-stat-advanced-scar-gel-30ml.
Vivier, V-STAT TM, Vivier Pharma Inc., May 24, 2017, https://www.vivierpharma.com/en_US/v-stat/.
Vivier, Vivier Pharma launches V-STAT Advanced Scar Gel, PR Web, May 24, 2017, https://www.prweb.com/releases/2017/05/prweb14362706.htm.
Spec-Chem Ind, China, 2014, pp. 1-2. (Year: 2014).
Aprahamian M. et al., "Effects of supplemental pantothenic acid on wound healing: experimental study in rabbit", Am J Clin Nutr. Mar. 1985: 41 (3):578-89 (abstract only is attached). (Year: 1985).

(Continued)

*Primary Examiner* — Kyung S Chang
(74) *Attorney, Agent, or Firm* — Julie Gauvreau; Lavery, de Billy, L.L.P.

(57) ABSTRACT

The present invention describes stable topical barrier compositions comprising primary polyamines and uses thereof for protecting the skin from external stressors, for improving skin's moisture and fort stimulating healing of the skin. These compositions may be used in a variety of cosmetic and therapeutic applications including for promoting wound healing, for reducing or preventing the formation of hypertrophic scar tissue, for reducing or preventing skin irritation and inflammation, for increasing skin's moisture and/or for reducing or preventing skin's signs of aging.

18 Claims, No Drawings

(56) References Cited

OTHER PUBLICATIONS

USPTO Restriction Requirement dated Jul. 2, 2020 in U.S. Appl. No. 16/883,864.
USPTO Non Final Rejection dated Nov. 12, 2020 in U.S. Appl. No. 16/883,864.
USPTO Restriction Requirement dated Aug. 10, 2022 in U.S. Appl. No. 17/302,527.
USPTO Non Final Rejection dated Jan. 19, 2023 in U.S. Appl. No. 17/302,527.
USPTO Final Rejection dated Dec. 13, 2023 in U.S. Appl. No. 17/302,527.

PUTRESCINE TOPICAL BARRIER FORMULATION

CROSS REFERENCE TO RELATED APPLICATIONS

This application is a continuation of U.S. application Ser. No. 17/302,527 filed on May 5, 2021, now pending which is a continuation of U.S. application Ser. No. 16/883,864 filed on May 26, 2020, now abandoned which is a continuation of U.S. application Ser. No. 16/349,030 filed on May 10, 2019, now abandoned, which is a National Entry Applications of PCT application no PCT/CA2018/050008 filed on Jan. 5, 2018 and published in English under PCT Article 21(2), which itself claims benefit of U.S. provisional application Ser. No. 62/443,158, filed on Jan. 6, 2017. All documents above are incorporated herein by reference in their entirety.

FIELD OF THE INVENTION

The present invention relates to stable, barrier and multi-function, multi-layer topical formulations comprising primary polyamines and uses thereof for stimulating wound healing, improving moisturization (prevention of Trans Epidermal Water Loss) and reducing skin inflammation, skin irritation and signs of aging. The present invention also relates to a process for obtaining such formulations.

BACKGROUND OF THE INVENTION

Skin is a physical barrier to the environment. In mammals, it is composed of multiple layers of ectodermal tissue, and guards the underlying muscles, bones, ligaments and internal organs. It is the alteration (damage) of the barrier properties that causes skin conditions.

The epidermis and the dermis, separated by the basal membrane, EDJ (Epidermal-Dermal Junction) or Grenz Zone, constitute the cutaneous covering on the hypoderm. The epidermis is the most superficial layer of the skin and provides its resistance and impermeability. Alteration of this layer will negatively affect perceived quality of the skin and will eventually lead to cutaneous aging. Lasers, retinoids, chemical peels, microdermabrasion, microneedling, skin exfoliants (glycolic, salicylic acid, AHAs///BHAs) cause thinning of the skin. The dermis (the internal layer of the skin) is conjunctive tissue composed of cells (essentially fibroblasts) dispersed in a complex medium called the extracellular matrix (ECM). This matrix consists of collagen and elastin fibers, glycoproteins (fibronectin and laminin) and proteoglycans. The extracellular matrix serves as a structure for the cells, allowing tissues and organs to cohere in pluricellular organisms. The EDJ, which attaches the epidermis, and the dermis of the skin is vitally important due to the roles it plays in cellular communication, nutrient exchange and absorption, moisturization and other skin functions. The layers of the epidermis are continually moving upward, throwing their "contents" overboard, flattening, building up at the surface and then eventually sloughing off to make room for the cells right behind them. This natural movement or "keratinization" of the skin is an integral part of skin renewal and healing. It would not be possible without the Epidermal-Dermal Junction (EDJ) maintaining the relationship between the two main layers of skin, allowing for healthy communication from the top all the way to the bottom.

The EDJ is also responsible for the exchange of nutrients back and forth from the epidermis to the dermis. These nutrients are carried in the blood from the food we eat and absorbed through the pores from topical application. Vitamins, antioxidants, acids and other nutrients are needed for DNA repair, new cell production, protection from outside elements and oxidative stress and more. In youth, this junction is a healthy, wavy terrain. The finger-like waves in the junction, called rete ridges, form the interlocking connection between the dermis and epidermis. They increase the surface area of the epidermis that is exposed to these blood vessels and the needed nutrients. Without this nutrient exchange, skin would suffer premature aging and damage.

As we age or stress our skin, it tends to flatten out. If the junction completely flat lines, no pun intended, the communication and nutrient exchange comes to a halt. So, in order to maintain skin healthy—and youthful—you want to keep the communication open and the EDJ's rete waves as wavy as possible. Maintaining EDJ functioning can be helped by proper diet and topical skin supplementation as well as limiting over exfoliation, over exposure to harsh elements and any other form of stress or trauma.

Dry skin is one of the most common skin problems. It can be treated by applying moisturizers. Moisturizers are oily substances which are used to replace natural skin oils, to cover tiny fissures and to provide a protective film. Four types of moisturizers have been described according to their mechanism of action: Occlusive, Humectants, Emollients, and Protein Rejuvenators. Occlusive moisturizers (e.g., petroleum in a minimum concentration of 5%, lanolin, mineral oil, silicones (such as dimethicone)) are substances which physically block Trans-Epidermal Water Loss (TEWL) in the stratum corneum. Humectants (e.g., glycerin, sorbitol, urea, alpha-hydroxy acids, and other sugars) work by attracting trans-epidermal water to the skin to improve hydration of the stratum corneum. Emollients (e.g., Vitamin E, fatty acids, cholesterol, squalene, structural lipids (e.g., ceramide), stearic, linoleic, linolenic and lauric acids (found in palm oil and coconut oil) smooth skin by filling spaces between skin flakes and droplets of oil. Some emollients (long chain fatty acids) act by influencing skin's physiology and pathology through their action on skin barrier function, eicosanoid production, cell signaling and membrane fluidity. Moisturizers containing collagen and other large proteins (e.g., elastin and keratin) are said to rejuvenate the skin by providing essential proteins (however, efficient dermal delivery of such proteins often remains a challenge due to their large size). Moisturizers and their effects are reviewed in C. W. Lynde. Moisturizers: What they are and how they work. Skin Therapy Letter, 2001; www.skintherapyletter-.com/2001/6.13/2.html.

Cutaneous aging is a complex phenomenon responsible for progressive changes of the skin. Aging of the skin results from two processes: (1) an intrinsic process, corresponding to chronological aging, and (2) an extrinsic process resulting mainly from the deleterious effect of exposure to environmental stresses. Genetic background, UV exposure, climatic factors (harshness/wind/cold/warm), pollution (chemical, free radicals, contaminant, nitrogen oxide, metals), alcohol consumption and smoking are factors involved in cutaneous aging.

Scar tissue is formed during healing of wounds following for example traumatic injury, burn and surgery (including cosmetic surgery). Often unpredictably, hypertrophy of the scar tissue occurs. Hypertrophic scar formation is characterized by the accumulation of collagen type III out of proportion to collagen type I. During skin wound healing it appears that type III procollagen amino peptide (PIIP) is cross-linked to other components of the wound matrix, such as fibrin and fibronectin, by tissue transglutaminase. Such cross-linking is thought to contribute to tissue hypertrophy and disproportionate scarring. Common treatment of hypertrophic scar tissue includes the use of drugs with potentially serious side effects (e.g., corticosteroid injection) and invasive procedures including surgical excision or cryotherapy.

Human growth factors (HGFs) have been attributed to many rejuvenating properties and are used as anti-aging agents and alternative wound healers. Many growth factors such as EGF and TGF-B are large proteins, which do not penetrate the skin well. They are also very unstable and often lose their activity within days in water or even as solids at normal temperatures. Furthermore, there are more and more concerns that at certain concentrations and over certain durations of application they can cause cells to over-proliferate and increase the risk of developing cancer and other health problems.

Primary polyamines (polyazaalkanes) have long been known as antioxidants. Recently, these compounds are attracting more and more interest as they have been shown to reduce skin inflammation and irritation and to be highly effective wound healing agents. Their effect on wound healing and hypertrophic scarring is thought to be due, at least partly, to their transglutaminase inhibiting activity which reduces type III pro-collagen cross-linking to components of the wound extracellular matrix. In addition to their effects on skin irritation, inflammation and on wound healing, primary polyamines have also been identified as useful agents to prevent and/or reduce the skin's signs of aging (see for example U.S. Pat. No. 5,885,982, CA 2 706 630 and WO 2009/067799).

Examples of primary polyamines include aminoacetonitrile, dansylcadaverine (1,5-diaminopentane), spermidine, and putrescine (1,4-diaminobutane (1,4-DAB)). Putrescine is a natural compound that is related to cadaverine; both are produced by the breakdown of amino acids in living and dead organisms. The two compounds are largely responsible for the foul odor of putrefying flesh but are also found in other conditions (e.g., bad breath). They are also found in semen and some microalgae, together with related molecules like spermine and spermidine. Putrescine is synthesized in small quantities by healthy living cells by the action of ornithine decarboxylase.

U.S. Pat. No. 5,885,982 (Dolynchuk) describes a method of preventing hypertrophic scarring in human dermal wounds by applying a topical inhibitor of fibroblast tissue transglutaminase. Putrescine was shown to reduce collagen cross-linking in vitro and in vivo resulting in a softer and a more rapidly mature-looking scar as compared to controls. The negative side effects, typical of steroid injection, were not seen. Studies done on human harvested scars revealed an increase in apoptosis of scar fibroblasts which lead to a less active scar than seen with other methods of treatment.

Canadian patent application CA 2,706,630 (Dolynchuk, K.) further shows that putrescine provides beneficial effects on the epidermis of eroded skin increasing its barrier function as well as the thickness of the stratum lucidum in animals and the inner strata of human epidermis. The presence of topical polyamines such as putrescine enhances the cellular regenerative mechanisms and creates a robust Grenz layer. These are typically reduced by inflammation, steroids and aging effects, the recovery of which, results in a more youthful looking and functionally stable skin.

Vitamin C (also known as Ascorbic Acid) is another well-known powerful antiaging and wound healing agent. Vitamin C deficiency causes spontaneous breakdown of wounds in the absence of infection in many surgery patients. Furthermore, evidence from the scientific literature shows that Vitamin C can increase collagen production in skin fibroblasts[1], counter skin damage associated with photo aging[2] and reduce the inflammation and erythema of sunburn[3]. Ultimately Vitamin C helps reduce the expression of skin aging, translated into the appearance of fine lines or wrinkles in the skin.

In mammals, Vitamin C is involved in all phases of wound healing. It is necessary for a normal response to physiological stressors, with this need increasing during times of injury. Events that cause wounding, including trauma or surgery are physiological stressors that have been associated with a decrease in blood plasma Vitamin C levels. In the inflammatory phase it is required for neutrophil apoptosis and clearance. During the proliferative phase, Vitamin C has been shown to regulate synthesis, maturation, secretion and degradation of collagen. Also, evidence suggests that Vitamin C may improve wound healing by stimulating quiescent fibroblasts to divide and by promoting their migration into the wounded area. Furthermore, studies have shown that Vitamin C protects the skin by increasing the capacity of fibroblasts to repair potentially mutagenic DNA lesions and acts as a powerful antioxidant and immune system modulator.

The numerous beneficial effects attributed to Vitamin C make it a particularly remarkable active agent in cosmetic and wound healing applications. Humans lack the ability to store Vitamin C, so it is important to continually replenish this vitamin through dietary means and/or other means such as topical supplementation (MacKay, Douglas, N D, and Miller, Alan L., ND, 2003).

Although a variety of chemical forms of Vitamin C are available commercially, not all forms are equally absorbed or active. As an antioxidant, Vitamin C needs to remain in its unoxidized form in order to be effective. However, it is particularly subject to oxidative degradation. Vitamin C is not lipophilic and is thus much less soluble in glycols such as propylene glycol (50 mg/ml) and even in alcohols such as ethanol (10 mg/ml in absolute ethanol), but liposoluble derivatives have been identified (e.g., Ascorbyl palmitate, Tetra-isopalmitoyl ascorbic acid (IPAA) 3-0 Ethyl Ascorbic Acid, MAP (Magnesium Ascorbyl Phosphate), SAP (Sodium ascorbyl phosphate)). The problem to be solved with Ascorbic Acid formulations has thus always been to find a compromise between solubilization and stability. Furthermore, because of its sensitivity, it can be a challenge to combine Vitamin C (especially in high concentrations) with certain active ingredients, while maintaining adequate stability, solubility and activity of all components in the formulation.

The creation of stable topical skin care compositions thus often presents many difficulties and challenges due to the nature of the active ingredients and unpredictable interactions between components in the final formulation. Another important challenge in the field of topical formulations (cosmetic and therapeutic) remains the ability to deliver active ingredients into the skin to reach target cells and provide biological effects. Factors that influence skin penetration of a given active ingredient are numerous and include size of the molecule, its lipophilic/hydrophilic nature, polarity, interactions with other components in the composition and skin condition.

Despite the number of solutions that have been proposed, there thus remains a need for novel skin care compositions and methods of use thereof.

SUMMARY OF THE INVENTION

Provided herein is stable barrier formulation which place a physical barrier between the skin and contaminants (e.g., microorganisms and chemical and/or allergenic substances) or environmental stressors (pollution, sun, wind, etc.) which may irritate the skin or compromise its structural integrity or the healing process. In addition to its barrier protective function, the formulation advantageously comprises active ingredients (e.g., primary polyamines such as putrescine and optionally other ingredients) which stimulate skin's healing, help maintain and/or increase skin's moisture and prevent and/or reduce the formation of hypertrophic scar tissue. These formulations may be used in therapeutic and cosmetic applications and are particularly useful in preventing and reducing skin's signs of aging, skin irritation and inflammation, promoting wound healing and/or reducing the development of scar tissue, including hypertrophic scar tissue. The barrier formulations are thus particularly useful on sensitive, irritated, inflamed, cracked, chapped and/or wounded skin.

The barrier formulations of the present invention are of the "water-repellent" type (i.e., non-aqueous and do not have a pH) and are generally provided as an ointment. More specifically, barrier compositions of the present invention which contain at least one polyamine (e.g., Polyamine-DAB™ or 1,4-Diaminobutane) and optionally other active ingredients (e.g., Vitamin C, lanolin, glycerin, bisabolol (e.g., (−)-alpha-bisabolol (CAS 23089-26-1) and CAS 515-69-5 (+/−)-alpha-bisabolol)) encourages the natural regenerating process, accelerate healing, promote new cell growth, increase healthy blood flow, boost collagen and moisture levels in the skin and importantly, provide a physical barrier against chemical and environmental stressors.

In an aspect, compositions of the present invention focus on reducing inflammation and promoting skin's healing, resulting in beautiful and optimized skin results.

In a first aspect, the present invention thus provides a topical barrier (protective) composition comprising at least one primary polyamine (e.g., putrescine) in a water-repellent base (petroleum jelly and mineral oil base). The primary polyamine is preferably encapsulated in triglyceride phospholipids, similar to phospholipids that occur naturally in the body. Non-limiting examples of useful phospholipids for encapsulating the primary polyamine include phospholipids derived from coconut oil (e.g., composed predominantly of diester and triester phosphatides e.g., Coco phosphatidyl PG-dimonium chloride and Cocamidopropyl phosphatidyl PG-dimonium chloride), soy, rapeseed, eggs and borage. More specific examples include Stearamidopropyl phosphatidyl PG-dimonium chloride (from Palm oil), Linoleamidopropyl phosphatidyl PG-dimonium chloride (Safflower), γ-Linolenamidopropyl phosphatidyl PG-dimonium chloride (Borage), Sodium borageamidopropyl PG-dimonium chloride phosphate (borage (e.g., Cola™ Lipid BP)). Preferably, phospholipids used to encapsulate and stabilize the primary polyamine also has antimicrobial activity (see for example, Biomimetic phospholipids: Components for self-preservation (chapter 6, pp. 139-158) and Fatty Acids and Esters as multifunctional Components (Chapter 5, pp. 119-138) in Preservative-free and self-preserving cosmetics and drugs. Principles and Practice. Edited by Jon J. Kabara and Donald S. Orth. Cosmetic science and technology series; v. 16 (1997).

In embodiments, the phospholipid is in a concentration of between about 1% w/w and about 10% w/w. In embodiments, the phospholipid is in a concentration of between about 1% w/w and about 6% w/w. In embodiments, the phospholipid is in a concentration of between about 3% w/w and about 6% w/w. In embodiments, the phospholipid is in a concentration of about 4% w/w. Of course, the concentration of phospholipid used depends on the amount of primary polyamine to encapsulate and stabilize. The more primary polyamine is included in the topical composition, the more phospholipids are needed to solubilize, encapsulate and stabilize the primary polyamine In embodiments, the phospholipid is a quaternary ammonium salt which encapsulates (solubilizes) the primary polyamine and acts as a stabilizer. In embodiments, the quaternary ammonium salt is cocamidopropyl PG-dimonium chloride phosphate. In embodiments, the cocamidopropyl PG-dimonium chloride phosphate is in a concentration of between about 1% w/w and about 6% w/w. In embodiments, the cocamidopropyl PG-dimonium chloride phosphate is in a concentration of between about 3% w/w and about 6% w/w. In embodiments, the cocamidopropyl PG-dimonium chloride phosphate is in a concentration of about 4% w/w. Of course, the concentration of phospholipid used depends on the amount of primary polyamine to encapsulate. The more primary polyamine is included in the topical composition, the more phospholipids are needed to solubilize, encapsulate and stabilize the primary polyamine.

In embodiments, the primary polyamine is a primary aliphatic lower-alkyl (C1-5) monoamine; a primary aliphatic alkylamine; or a primary aliphatic lower-alkyl (C1-5) polyamine. In embodiments, the primary aliphatic lower-alkyl (C1-5) monoamine is aminoacetonitrile, the primary aliphatic alkylamine is spermine or spermidine and the primary aliphatic lower-alkyl (C1-5) polyamine is putrescine or dansylcadaverine. In preferred embodiments, the primary aliphatic lower-alkyl (C1-5) polyamine comprises or consists of putrescine.

In embodiments, the putrescine is in a concentration of between about 0.1% w/w to about 1% w/w. In embodiments, the putrescine is in a concentration of about 0.4% w/w. In embodiments, the putrescine is in a concentration of about 0.8% w/w.

In embodiments, the petroleum jelly in the barrier composition of the present invention is in a concentration of between about 25% w/w and 65% w/w, preferably between 35% w/w and 55% w/w. In embodiments, the petroleum jelly in the barrier composition of the present invention is in a concentration of between about 40% w/w and 50% w/w. In embodiments, the petroleum jelly is in a concentration of about 45% w/w.

In embodiments, the mineral oil in the barrier composition of the present invention is in a concentration of between about 30% w/w and about 50% w/w. In embodiments, the mineral oil in the barrier composition of the present invention is in a concentration of between about 34% w/w and about 50% w/w. In embodiments, the mineral oil in the barrier composition of the present invention is in a concentration of between about 30% w/w and about 40% w/w. In embodiments, the mineral oil is in a concentration of about 35% w/w.

In embodiments, the barrier composition of the present invention further comprises paraffin. In embodiments, the barrier composition of the present invention further comprises paraffin. In embodiments, the paraffin wax is in a concentration of between about 0% w/w and 15% w/w, preferably between 0% w/w and up to 10% w/w, In embodiments, the paraffin wax is in a concentration of between about 3% w/w and 15% w/w. In embodiments, the paraffin wax is in a concentration of between about 6% w/w and 9% w/w (6%, 7%, 8%, 9%). In embodiments, the paraffin wax is in a concentration of about 8.5% w/w. In embodiments, the paraffin is ceresin wax.

In embodiments, the barrier composition of the present invention further comprises lanolin oil. In embodiments, the lanolin oil is in a concentration of between about 3% w/w and 6% w/w (3%, 4%, 5% and 6%). In embodiments, the lanolin oil is in a concentration of about 5% w/w.

In embodiments, the barrier composition of the present invention further comprises a lipophilic Vitamin C derivative. In embodiments, the lipophilic Vitamin C derivative is in a concentration of between about 0.% w/w and 10% w/w (i.e., up to 10%). In embodiments, the lipophilic Vitamin C derivative is in a concentration of between about 0.1% w/w and 10% w/w. In embodiments, the lipophilic Vitamin C derivative comprises Ascorbyl palmitate. In embodiments, the Ascorbyl palmitate is in a concentration of about 0.5% w/w. In embodiments, the lipophilic Vitamin C derivative comprises 3-O-Ethyl Ascorbic Acid (3-OEAA). In embodiments, the 3-O-EAA is in a concentration of about 0.5% w/w. In embodiments, the 3-O-EAA is in a concentration of about 1% w/w. In embodiments, the 3-O-EAA is in a concentration of about 2% w/w. In embodiments, the 3-O-EAA is in a concentration of about 5% w/w.

In embodiments, the barrier composition of the present invention further comprises one or more humectants. In embodiments, the humectants are in a concentration of between about 0.5% w/w and 3% w/w. In embodiments, the humectants comprise glycerin, Vitamin B5 or a combination thereof. In embodiments, the humectants comprise about 1% w/w of said glycerin and about 1% w/w of said Vitamin B5.

In embodiments, the barrier composition of the present invention further comprises bisabolol. In embodiments, the bisabolol is in a concentration of between about 0.1% w/w and 1% w/w. In embodiments, the bisabolol is in a concentration of about 0.5% w/w.

In embodiments, the above-noted barrier compositions are for treating or preventing skin inflammation, skin irritation and/or skin's signs of aging. In embodiments, the barrier compositions of the present invention are for promoting wound healing. In embodiments, the barrier compositions of the present invention are for preventing or reducing the formation of hypertrophic scar tissue.

In a related aspect, the present invention concerns the use of the above-noted barrier compositions (i) for treating or preventing skin inflammation, skin irritation and/or skin's sign of aging; (ii) for promoting wound healing; and/or (iii) for preventing or reducing the formation of hypertrophic scar tissue.

More specifically there are provided the following items:
1. A topical water free barrier composition comprising: (i) a primary polyamine; (ii) a phospholipid to encapsulate the primary polyamine; (iii) petroleum jelly; and (iv) mineral oil.
2. The barrier composition of item 1, wherein the primary polyamine is a primary aliphatic lower-alkyl (C1-5) monoamine; a primary aliphatic alkylamine; or a primary aliphatic lower-alkyl (C1-5) polyamine.
3. The barrier composition of item 2, wherein the primary aliphatic lower-alkyl (C1-5) monoamine is aminoacetonitrile, the primary aliphatic alkylamine is spermine or spermidine and the primary aliphatic lower-alkyl (C1-5) polyamine is putrescine or dansylcadaverine.
4. The barrier composition of item 1 or 2, wherein the primary polyamine is aminoacetonitrile.
5. The barrier composition of item 1 or 2, wherein the primary polyamine is spermine or spermidine.
6. The barrier composition of item 1 or 2, wherein the primary polyamine is putrescine or dansylcadaverine.
7. The barrier composition of item 1 or 2, wherein the primary polyamine is putrescine.
8. The barrier composition of item 7, wherein the putrescine is in a concentration of between about 0.1% w/w to about 1% w/w.
9. The barrier composition of item 8, wherein the putrescine is in a concentration of about 0.4% w/w.
10. The barrier composition of item 8, wherein the putrescine is in a concentration of about 0.8% w/w.
11. The barrier composition of any one of items 1 to 10, wherein the petroleum jelly is in a concentration of between about 25% w/w and 65% w/w.
12. The barrier composition of item 11, wherein the petroleum jelly is in a concentration of about 45% w/w.
13. The barrier composition of any one of items 1 to 12, wherein the mineral oil is in a concentration of between about 30% w/w and about 45% w/w.
14. The composition of item 13, wherein the mineral oil is in a concentration of about 35% w/w.
15. The barrier composition of any one of items 1 to 14, wherein the phospholipid is a quaternary ammonium salt.
16. The barrier composition of item 15, wherein the quaternary ammonium salt is cocamidopropyl PG-dimonium chloride phosphate.
17. The barrier composition of item 16, wherein the cocamidopropyl PG-dimonium chloride phosphate is in a concentration of between about 3% w/w and about 6% w/w.
18. The barrier composition of item 17, wherein the cocamidopropyl PG-dimonium chloride phosphate is in a concentration of about 4% w/w.
19. The barrier composition of any one of items 1 to 18, further comprising paraffin.
20. The barrier composition of item 19, wherein the paraffin is in a concentration of between about 3% w/w and 15% w/w.
21. The barrier composition of item 20, wherein the paraffin is ceresin wax and is in a concentration of about 8.5% w/w.
22. The barrier composition of any one of items 1 to 21, further comprising lanolin oil.
23. The barrier composition of item 22, wherein the lanolin oil is in a concentration of between about 3% w/w and 6% w/w.
24. The barrier composition of item 23, wherein the lanolin oil is in a concentration of about 5% w/w.
25. The barrier composition of any one of items 1 to 24, further comprising a lipophilic Vitamin C derivative.
26. The composition of item 25, wherein the lipophilic Vitamin C derivative is in a concentration of between about 0.1% w/w and 10% w/w.
27. The composition of item 25 or 26, wherein the lipophilic Vitamin C derivative comprises 3-O-Ethyl Ascorbic Acid (3-O-EAA).
28. The composition of item 27, wherein the 3-O-EAA is in a concentration of about 0.5% w/w.
29. The barrier composition of any one of items 1 to 28, further comprising one or more humectants.
30. The barrier composition of item 29, wherein the humectants is in a concentration of between about 0.5% w/w and 3% w/w.
31. The barrier composition of item 29 or 30, wherein the humectants comprise glycerin, Vitamin B5 or a combination thereof.

32. The barrier composition of item 31, wherein the humectants comprise about 1% w/w of the glycerin and about 1% w/w of the Vitamin B5.
33. The barrier composition of any one of items 1 to 32, further comprising bisabolol.
34. The barrier composition of item 33, wherein the bisabolol is in a concentration of between about 0.1% w/w and 1% w/w.
35. The barrier composition of item 34, wherein the bisabolol is in a concentration of about 0.5% w/w.
36. The barrier composition of any one of items 1 to 35, for treating or preventing skin inflammation, skin irritation.
37. The barrier composition of any one of items 1 to 36, for promoting wound healing.
38. The barrier composition of any one of items 1 to 36, for preventing or reducing the formation of hypertrophic scar tissue.
39. Use of the barrier composition defined in any one of items 1 to 36, for treating or preventing skin inflammation, skin's signs of aging and/or skin irritation.
40. Use of the barrier composition defined in any one of items 1 to 36, for promoting wound healing.
41. Use of the barrier composition as defined in any one of items 1 to 36, for preventing or reducing the formation of hypertrophic scar tissue.

DESCRIPTION OF ILLUSTRATIVE EMBODIMENTS

Not all cosmetic products are alike. Important factors affecting cosmetic and therapeutic results include the stability of the active ingredient(s) in the compositions, their solubility in the desired carrier and their ability to penetrate the skin and reach its targeted layer(s). Applicants have developed new non-aqueous (substantially water free) topical barrier compositions in which the active ingredients (e.g., putrescine and derivatives thereof) are stable and soluble in an ointment-like base, thereby protecting the skin from external irritants and contaminants and enabling the active ingredients to reach the cells and provide the desired effect.

A key ingredient of the composition of the present invention is a polyamine such as 1,4-Diaminobutane Dihydrochloride (also called Putrescine Dihydrochloride, or 1,4-DAB). The 1,4-DAB molecule has unique cellular properties. It promotes healing and repair at the cellular level, preserves skin elasticity and enhances skin smoothness. 1,4-DAB may lengthen the lifespan of a skin cell and thicken cellular matrix to rejuvenate skin, and therefore may reduce downtime for patients after skin treatment such as laser or peeling, or after cosmetic surgery intervention (ex. Eyelift, breast augmentation).

1,4-DAB, is a highly reactive basic amine salt. It reacts easily with acidic compounds and is thus not very stable. Due to their polar nature, salts such as 1,4-DAB do not usually dissolve in ointment because they need water, which ointment base lacks. Even when they do, they generally become unstable.

Applicants have found that by encapsulating the primary polyamine (e.g., 1,4-DAB) in a phospholipid such as PG-Dimonium Chloride Phosphate, a stable ointment could be prepared. The encapsulation allows to dissolve the polyamine in an ointment base to provide a homogenous, stable composition.

Encapsulation in phospholipids such as PG-Dimonium Chloride Phosphate stabilizes the primary polyamine and prevents it from reacting with other ingredients in the ointment, thereby avoiding discoloration of the composition and preserving therapeutic and cosmetic activity. Encapsulation further facilitates delivery of the primary polyamine into the skin.

Applicants have further found that stability of the ointment composition comprising a primary polyamine and Vitamin C could be further improved by using certain forms of Vitamin C derivatives over others. Indeed, L-Ascorbic Acid was difficult to combine with a primary polyamine, even when encapsulated. Moreover, even when liposoluble forms of vitamin C were used, it was found that the stability of the composition could be significantly improved by using 3-O-Ethyl Ascorbic Acid (3-O-EAA) instead of other forms of liposoluble vitamin C derivatives such as ascorbyl palmitate. Compositions comprising a combination of a primary polyamine (e.g., 1,4-DAB) and 3-O-EAA in an ointment base were found to be most stable.

Topical barrier compositions of the present invention were found to allow proper dissolution of active ingredients (e.g., polyamines) and to be stable thereby enabling the effective penetration and delivery of active ingredients into the skin.

In a first aspect, the present invention provides a topical barrier composition comprising (i) at least one primary polyamine (e.g., putrescine) in an ointment-like base comprising (ii) petroleum jelly; and (iii) mineral oil. The primary polyamine is encapsulated in phospholipids (e.g., cocamidopropyl PG-diimonium chloride phosphate). In embodiments, the active ingredient further comprises lanolin, glycerin, bisabolol, panthenol and/or a liposoluble Vitamin C derivative.

The primary polyamines used in accordance with the present invention are preferably amine group terminated linear structures such as unbranched aliphatic compounds (e.g., lower C1-C10, preferably, C1-C5 alkyls). Such compounds include, but are not limited to naturally occurring putrescine (1,4-diaminobutane (Cas #333-93-7), $H_2N(CH_2)_4NH_2$), cadaverine (Cas #462-94-2, 1,5-pentanediamine, $H_2N(CH_2)_5NH_2$), spermidine (Cas #124-20-9, 1,4-butanediamine, N1-(3-aminopropyl, $H_2N(CH_2)_3NH(CH_2)_4NH_2$), spermine (Cas #71-44-3, 1,4-Butanediamine, N,N'-bis(3-aminopropyl), $H_2N(CH_2)_3NH(CH_2)_4\ NH(CH_2)_3NH_2$) and their functional derivatives. The polyamines preferably have $(CH_2)_n$ groups linking the nitrogen atoms where n is 2 to 10, preferably 2 to 6, more preferably 2 to 5 and particularly ones comprising 2 to 6 nitrogen atoms, particularly 2, 3 or 4 nitrogen atoms. These polyamines are available from natural sources, e.g., mammalian semen or fermentation products (for example from soy or anchovies), or may be manufactured by conventional techniques, e.g., solid state polypeptide production followed by amidation and reduction. Polyamines useful in accordance with the present invention are described for example in WO2006/048671, U.S. Pat. No. 5,885,982 and CA 2,706,630. The polyamine (s) used in accordance with the invention may conveniently be in salt form with a physiologically tolerable counterion, (e.g., inorganic/mineral acid, an organic acid such as an alpha-hydroxyacid or a fatty acid). Such salts may be prepared by reaction of the polyamine and the acid, e.g., in solution in approximately equimolar amounts.

Under certain aspects, the total polyamine content in the compositions of the present invention is between about 0.0005 and about 5% w/w (e.g., between about 0.001% w/w and about 1% w/w, between about 0.005% w/w and about 1% w/w, between about 0.1% w/w and about 1% w/w.). Preferably, in compositions for use in stimulating wound healing (e.g., reducing the appearance of scar tissue, including hypertrophic scar tissue), the concentration of putrescine is preferably between about 0.1% w/w and about 1% w/w, more preferably between about 0.4% w/w and about 0.8% w/w.

Advantageously, the barrier compositions of the present invention comprise phospholipids (e.g., a quaternary ammonium salt) which encapsulates and helps to stabilize and solubilize the primary polyamine. Non-limiting examples of solubilizers for primary polyamines which may be used in the barrier composition of the present invention include cocamidopropyl PG-dimonium chloride phosphate. In embodiments, for a concentration of putrescine of about 0.8% w/w, compositions of the present invention comprise between about 1% and about 6%, preferably between about 3% w/w and about 6% w/w of phospholipids (e.g., quaternary ammonium salt acting as a solubilizer/stabilizer). In embodiments, the phospholipid (solubilizer/stabilizer) is cocamidopropyl PG-dimonium chloride phosphate. In particular embodiments, the barrier compositions of the present invention comprise about 4% of cocamidopropyl PG-dimonium chloride phosphate.

In the barrier compositions of the present invention, active ingredients are solubilized in a non-aqueous (water-insoluble) "barrier" base which comprises petroleum jelly, and/or mineral oil. In addition to its film-forming properties, which avoid contact with exterior irritants and contaminants, the base also contributes to healing and moisturization the skin. For example, a verified medicinal use of petroleum jelly is to protect and prevent moisture loss of the skin of patients in the initial post-operative period following laser skin resurfacing (Khan, Jemshed A. (2008). "CO2 Laser Resurfacing Immediate Postoperative Care Prior to Complete Epithelialization". In Hartstein, Morris E.; Holds, John B.; Massry, Guy G. Pearls and Pitfalls in Cosmetic Oculoplastic Surgery. p. 417. doi:10.1007/978-0-387-69007-0_136. ISBN 978-0-387-25389-3 and Jeong, Jeung-Tae; Kye, Young-Chul (2001). "Resurfacing of Pitted Facial Acne Scars with a Long-Pulsed Er:YAG Laser". Dermatologic Surgery. 27 (2): 107-10. doi:10.1046/j.1524-4725.2001.00201.x. PMID 11207680). It is also largely used to moisturize skin and combat cracking of the skin (e.g., chapped skin). Mineral oil is also one of the safest, most non-sensitizing moisturization ingredients found. Both ingredients are among the most effective and inert moisturization ingredients available.

In embodiments, the barrier compositions of the present invention comprise between about 25% w/w and about 65% w/w of petroleum jelly (25%, 26%, 27%, 28%, 29%, 30%, 31%, 31%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, or 65%). In embodiments, the barrier compositions comprise between about 40% w/w and 50% w/w of petroleum jelly. In particular embodiments, the barrier compositions comprise about 45% w/w of petroleum jelly.

In embodiments, the barrier compositions of the present invention comprise between about 25% w/w and about 45% w/w of mineral oil. In embodiments, the barrier composition comprises between about 30% w/w and 50% w/w of mineral oil. In embodiments, the barrier composition comprises about 35% w/w of mineral oil. In particular embodiments, the barrier composition comprises about 34% w/w of mineral oil.

In addition to petroleum jelly and mineral oil, the barrier composition of the present invention may also comprise a wax (e.g., paraffin such as ceresin wax). The wax is used as a thickener and stabilizer. In embodiments, the barrier compositions of the present invention comprise between about 3% w/w and about 15% w/w of wax. In embodiments, the barrier composition comprises between about 7% w/w and about 10% w/w of wax. In particular embodiments, the barrier composition of the present invention comprises about 8.5% w/w of wax. In embodiments, the wax is paraffin. In embodiments, the paraffin is cerasin. In embodiments, the barrier composition of the present invention comprises about 8.6% of paraffin.

In embodiments, the barrier compositions of the present invention further advantageously comprise Lanolin. Lanolin's beneficial effects on the human skin and hair have been known and valued by humans for thousands of years. This natural emollient is absorbed by the skin, and is said to help restore its correct moisture balance and softness without impairing natural skin functions. To prevent the intercellular water from evaporation, lanolin lipids form a semi-occlusive film on the skin and create a protective barrier. Accordingly, in embodiments, the barrier composition of the present invention comprise between about 2% w/w and about 10% w/w of lanolin, preferably between 3% w/w and 6% w/w. In particular embodiments, barrier compositions of the present invention comprise between 4% w/w and 5% w/w of lanolin.

In embodiments, the barrier composition of the present invention preferably further comprises one or more humectants (moisturization ingredients). Preferably, the one or more humectants comprise glycerin and/or Vitamin B5 (panthenol). Humectants such as glycerin and panthenol have the ability to draw water from the environment and the dermis (the lower layers of the skin) into the outer (surface) layer of the skin. They also help to keep the skin barrier intact. Thus, in embodiments, the barrier compositions of the present invention comprise between 0.25% and 15% w/w of an humectant. In embodiments, between zero and 5% w/w, preferably between and 3% w/w of humectants (e.g., glycerin and/or panthenol). In particular embodiments, the barrier compositions of the present invention comprise about 1% w/w of glycerin and about 1% w/w of panthenol.

Compositions of the present invention may also advantageously include bisabolol. Bisabolol is a scent ingredient naturally occurring in camomile. It is known to have anti-irritant, anti-inflammatory and anti-microbial properties. Bisabolol was also demonstrated to enhance the percutaneous absorption of certain molecules (J Am Oil Chem. Soc. (2010) 87; 1-7). In embodiments, barrier compositions of the present invention comprise between about 0.01 and 2% w/w of bisabolol. In particular embodiments, about 0.5% w/w of bisabolol.

In certain aspects, compositions of the present invention additionally comprise a liposoluble Vitamin C derivative. As used herein, the expression "liposoluble Vitamin C derivative" refers to an Ascorbic Acid derivative which is liposoluble (e.g., soluble in the non-aqueous barrier composition of the present invention which comprises petroleum jelly and mineral oil). Non-limiting examples of suitable liposoluble Vitamin C derivatives include: Ascorbyl palmitate (AA-PAL), Ascorbyl-6-caprylate, ascorbyl-6-laurate and Ascorbyl tetra-isopalmitate (VC-IP), 3-O-Ethyl Ascorbic Acid (3-O-EAA). In an embodiment, such liposoluble Vitamin C derivative is Ascorbyl palmitate and/or Tetra-isopalmitoyl Ascorbic acid (IPAA). In particular embodiments, compositions of the present invention comprise more than zero and up to about 10% w/w of a liposoluble Vitamin C derivative. In embodiments, about 10% w/w, about 5% w/w, about 2% w/w, about 1% w/w or about 0.5% w/w of a liposoluble Vitamin C derivative. Preferably, compositions of the present invention comprise at least about 0.5% w/w of a liposoluble Vitamin C derivative. In embodiments, the compositions comprise about 0.5% w/w of Ascorbyl palmitate.

Compositions of the present invention may additionally comprise one or more further active ingredients (e.g., useful for reducing or preventing skin aging, skin irritation and inflammation, for improving skin texture, skin tone and/or skin healing). As used herein, the term "active ingredient" refers to various types of optional additional active ingredients that may be used in compositions of the present invention. Actives are defined as skin benefit agents other than emollients and ingredients that merely improve the physical characteristics of the composition. Although not limited to this category, common examples include talcs and silicas, zinc salts, and sunscreens.

Non-limiting examples of active ingredients that may be added in compositions of the present invention include: retinol, resveratrol, polyphenol, *Pseudoalteromonas* ferment extract, hydrolyzed wheat protein, hydrolyzed soy protein, *Glycine soja* (soybean) protein, citrulline, tripeptide-1 (glycine,-histidine-lysine), tripeptide-5, palmitoyl tripeptide-5, tripeptide-8, tripeptide-10, glycine, *Butyrospermum parkii* (shea) butter, *Argania spinosa* kernel oil, jojoba esters, glucose, hydrolyzed rice protein, superoxide dismutase, *Rosmarinus officinalis* (rosemary) leaf extract, cetearyl olivate, sorbitan olivate, *Ruscus aculeatus* root extract, *Centella asiatica* extract, hydrolyzed yeast protein, hydrolyzed casein, *Calendula officinalis* flower extract, acetyl hexapeptide-3, allantoin, *Citrus grandis* (grapefruit) extract, hydrolyzed glycosaminoglycans, hyaluronic acid, acetylated hyaluronic acid, sodium hyaluronate, *Persea gratissima* (avocado) oil, tropolone, lysine HCII, *Porphyridium cruentum* extract, dimethiconol, caprylic/capric triglyceride, Cytokinol™, phytonadione (Vitamin K), Vitamin E (tocopherols (e.g., γ-tocopherol) and tocotrienols), escin, panthenol, Argireline, Kinetine, CE ferulic Acid, skin growth factors, Petrolatum/Canolin, dimethyl sulphoxide, coconut oil, keratolytic agents, unsaturated fatty acids (e.g., omega-3, omega-6 and omega-9 unsaturated fatty acids, especially omega-3 acids, for example EPA, DHA and ALA) and derivatives (particularly esters) thereof, HMG-CoA reductase inhibitors, natural triterpenes, Coenzyme Q10 (ubiquinone), Vitamin B3, hydroquinone (tocopheryl acetate), Aloe, *Mallotus japonicus* extract, hydroxyacids (e.g., alpha hydroxy acids such as glycolic acid), beta-(1,3) glucans, extract of unpolished rice, urea, pine seed oil, marine collagens, plant cell extracts, ceramides, cholesterol, glutathione, carnitine, caffeine, *Rosa mosqueta* oil, cystein derivatives, acid and alpha-amino acids, and salts of any of these.

In embodiments, compositions of the present invention comprise one or more further antioxidants. As used herein, the term "antioxidant" refers to compounds, natural or synthetic, capable of neutralizing reactive oxygen species (ROS). Commonly used antioxidants in compositions (dermatological compositions) include, for example, Ascorbic Acid (Vitamin C), tocopherol (Vitamin E), isoflavones, polyphenols, and retinoids, (including retinoic acid (0.25% to 0.1%), tretinoin, retinal, retinol (0.1% to 5%), Adapalene, tazorotene and retinyl esters. Reviewed in Sheri L. Rolewski. Dermatology Nursing. 2003; 15(5), Jannetti Publications, Inc.), alpha lipoic acid, beta-glucan, coenzyme Q10, grape seed extract, amino acids, green tea, soybean sterols, ergothioneine (EGT, a thiourea derivative of histidine), Resorcinol, Carcinine and mixtures thereof. In embodiments, compositions of the present invention comprise Vitamin C and at least one further antioxidant. In embodiments, compositions of the present invention further comprise (in addition to putrescine and/or Vitamin C) one or more of the following active ingredients: an antioxidant (e.g., a retinoid such as retinol), grapefruit extract, Vitamin E and/or hydroquinone. Generally, the concentration of retinoids (such as retinol) that may be used in accordance with the present invention is between about 0.01% and 5%.

Generally the total amount of active ingredients in compositions of the present invention may be up to 40% w/w of the composition. In embodiments, the total amount of active ingredients in compositions of the present invention is between about 0.1% w/w and about 35% w/w. In embodiments, the total amount of active ingredients is between about 0.1% and about 30% w/w. In embodiments, the total amount of active ingredients is up to 25% w/w of the composition. In embodiments, the total amount of active ingredients is up to 20% w/w of the composition.

The barrier compositions according to the invention may be in any form suitable for topical application, e.g., creams, ointments, balm, emulsions etc. and may if desired include a carrier substrate, e.g., a woven or nonwoven web. The compositions may contain conventional topical composition components, such as for example, solvents, oils (e.g., plant oils), aromas, sunscreens, colorants, viscosity modifiers, binders, diluents, emollients, thickeners, preservatives, stabilizers, humidifiers, skin penetration enhancers, vesicle wall formers, etc. Preferably, barrier compositions of the present invention are topical ointments.

Sunscreens include those materials commonly employed to block ultra-violet radiation. Illustrative compounds are the derivatives of para-aminobenzoic acid (PABA), cinnamate and salicylate. For example, avobenzophenone (Parsol 1789®), octyl methoxycinnamate and 2-hydroxy-4-methoxy benzophenone (also known as oxybenzone) can be used. 2-ethylhexyl-3-(4-methoxyphenyl)-2-propenoate, 2-phenyl-benzimidazole-5 sulphonic acid, and 2-hydroxy-4-methoxy benzophenone are commercially available under the trade-marks, Parsol MCX™, Parsol HS™ and Benzophenone-3™, respectively. The exact amount of sunscreen employed in the compositions can vary depending upon the degree of protection desired from the sun's ultra-violet radiation. Additives that reflect or scatter the sun rays may also be employed. These additives include oxides like zinc oxide and titanium dioxide.

Non-limiting examples of conventional topical composition components that may be included in barrier compositions of the present invention include lecithin, xanthan gum, carbomer, triethanolamine, phenoxyethanol, butylene glycol, caprylyl glycol, glyceryl stearate, PEG-100 stearate, PEG-75 stearate, PEG 40, dimethicone, glycerin, behenyl alcohol, cetyl palmitate, cyclopentasiloxane, dimethiconol, acrylates/acrylamide copolymer, magnesium aluminum silicate, methylparaben, ethylparaben, propylparaben, butylparaben, stearic acid, caprylic/capric triglyceride, titanium dioxide, triethoxycaprylylsilane, castor oil phosphate, tocopheryl acetate, tetrasodium edta, butylated hydroxy toluene, allyl methacrylates crosspolymer, polysorbate 20, carrageenan (*Chondrus crispus*), ethylhexylglycerin, cetyl alcohol, ceteth-20, steareth-20, pentylene glycol, sodium benzoate, sodium dextran sulfate, potassium sorbate, ammonium glycyrrhizate, ethoxydiglycol, propylene glycol, betaine, saccharide isomerate, trimethylolpropane, tricaprylate/tricaprate, cetyl alcohol, dmdm hydantoin, isobutylparaben, 1,2-hexanediol, 1,2-octanediol, hydrogenated palm glycerides, glyceryl polyacrylate, mineral oil, allyl methacrylate crosspolymer, polysorbate-85, glyceryl dilaurate, C13-14 isoparaffin, laureth-7, C12-13 pareth-23, hexamidine diisethionate, or benzoyl peroxide.

Many compositions may be protected against the growth of potentially harmful microorganisms. However, microorganisms generally don't grow or grow poorly in barrier compositions which comprise of no or only very small amounts of water. Nevertheless, anti-microbial compounds may be included in the compositions of the present invention. Suitable preservatives include alkyl esters of p-hydroxybenzoic acid (parabens), hydantoin derivatives, hexamidine diisethionate, propionate salts, parabens and a variety of quaternary ammonium compounds as well as chelating agents such as EDTA and well known antimicrobial non-parabens of all kinds.

Uses

Compositions of the present invention are intended to be used as is, or through the making of a composition or a medication, to prevent or to treat any skin condition that involves skin irritation or skin inflammation and to stimulate healing of wounded skin. The skin condition includes but is not limited to dermatitis, skin allergy, psoriasis, acne, eczema, rosacea, radiations exposure including U.V. or sun exposure, laser exposure, skin aging (e.g., reduction of wrinkles), dry skin, cracked or chapped skin, skin surgery and wound healing. Barrier compositions comprising putrescine are particularly useful for promoting wound healing and preventing and/or treating scars including hypertrophic scar tissue.

General Manufacturing Procedures

Compositions of the invention may be produced by standard cosmetic or pharmaceutical composition production techniques.

However, the process described in Examples 1 and 3 below, has been found particularly useful in preparing compositions of the present invention.

Other objects, advantages and features of the present invention will become more apparent upon reading the following non-restrictive description of specific embodiments thereof, given by way of example only.

Definitions

In order to provide clear and consistent understanding of the terms in the instant application, the following definitions are provided.

The articles "a," "an" and "the" are used herein to refer to one or to more than one (i.e., to at least one) of the grammatical object of the article.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps and are used interchangeably with, the phrases "including but not limited to" and "comprising but not limited to".

For the recitation of numeric ranges herein, each intervening number there between with the same degree of precision is explicitly contemplated. For example, for the range of 18-20, the numbers 18, 19 and 20 are explicitly contemplated, and for the range 6.0-7.0, the number 6.0, 6.1, 6.2, 6.3, 6.4, 6.5, 6.6, 6.7, 6.8, 6.9, and 7.0 are explicitly contemplated. The terms "such as" are used herein to mean, and is used interchangeably with, the phrase "such as but not limited to".

Unless otherwise defined herein, scientific and technical terms used in connection with the present disclosure shall have the meanings that are commonly understood by those of ordinary skill in the art. For example, any nomenclature used in connection with, and techniques of biochemistry, microbiology, chemistry and cosmetics described herein are those that are well known and commonly used in the art. The meaning and scope of the terms should be clear; in the event however of any latent ambiguity, definitions provided herein take precedent over any dictionary or extrinsic definition. Further, unless otherwise required by context, singular terms shall include pluralities and plural terms shall include the singular.

Practice of the methods, as well as preparation and use of the products and compositions disclosed herein employ, unless otherwise indicated, conventional techniques in chemistry and related fields as are within the skill of the art. These techniques are fully explained in the literature. See, for example The Handbook of Pharmaceutical Excipients, American Pharmaceutical Association, Washington (Editors Raymond C Rowe, Paul J. Sheskey and Siân C. Owen, 2006).

The term "substantially water-free" means very small amounts of water that are usually introduced into the composition along with the components and manufacturing process, such as less than 3%, preferably less than 2%, more preferably less than 1% by weight based on the weight of the total composition. For example, propyleneglycol may contain small amount of water (e.g., 0.2% water), and thus a small amount of water will usually be introduced into the composition along with certain ingredients such as propyleneglycol. Water may also be introduced into the composition by precipitation during the cooling phase of manufacturing. Preferably, the amount of water should be maintained below 2% and preferably less than 1%. Most preferably, no water is intentionally added to the composition.

An important excipient in the formulation is petrolatum, also commonly referred to as petroleum jelly. Petroleum jelly is usually obtained as the semisolid residue from petroleum after the lighter and more volatile components have been boiled off. The Handbook of Pharmaceutical Excipients, American Pharmaceutical Association, Washington (Editors Ainley Wade and Paul J Weller) Second Edition 1994, defines petroleum jelly as a purified mixture of semisolid saturated hydrocarbons having the general formula $C_{(n)}H_{(2n+2)}$ obtained from petroleum. The hydrocarbons comprise mainly branched and unbranched chains, although some cyclic alkanes and aromatic molecules with paraffin side chains may also be present. The term petroleum also includes other mixtures of petroleum based semisolid hydrocarbons that are commonly referred to in the art or commercially sold as "petroleum" or "petroleum jelly" that are suitable for application to skin. A common petroleum is sold under the trademark Vaseline. In the examples disclosed herein, a white petrolatum from Calumet has been utilized. If petrolatum from other manufacturers is used in the inventive formulation, the amounts disclosed herein may have to be slightly altered in order to achieve the desired properties of the formulation, which is well within the skill of one of ordinary skill in the art. Examples of other commercially available petrolatum include, but are not limited to, those from Ultra Chemical, Carolina Medical Products, Witco (Germany), and Amco Chemical.

The present invention is illustrated in further details by the following non-limiting examples.

EXAMPLE 1

Barrier Composition Comprising 0.4% Putrescine

The following barrier composition was prepared as described below.

TABLE 1

Barrier composition Formula A1 comprising 0.4% Putrescine.

| | Ingredients | CAS# | Grade | Amount (% W/W) |
|---|---|---|---|---|
| 1 | Petroleum Jelly (perfecta Petrolatum) | 8009-03-8 | USP | 47.00 |
| 2 | Mineral oil (white) | 8042-47-5 | USP | 35.30 |
| 3 | Paraffin (ceresin wax 130/135) | 8001-75-0 | MFR | 9.00 |
| 4 | Lanolin oil | 70321-63-0/ 8038-43-5 | MFR | 4.80 |
| 5 | Bisabolol | 23089-26-1 | USP | 0.50 |
| 6 | Putrescine (1, 4-diaminobutane) | 110-60-1 or 333-93-7 | MFR | 0.40 |
| 7 | Cocamidopropyl PG-Dimonium Chloride Phosphate | 83682-78-4 | MFR | 1.00 |
| 8 | Glycerin | 56-81-5 | USP | 1.00 |
| 9 | Panthenol (DL) | 16485-10-2 | MFR | 1.00 |
| | | | | 100% |

The above composition was prepared by adding and mixing the ingredients as follows in a stainless steel tank equipped with a lightening-type propeller mixer.

TABLE 2

Manufacturing procedure of Formula A1.

Step# Manufacturing Procedure

1. In a double jacketed stainless steel tank equipped with a lightening type propeller add ingredients identified as 1 to 5 (PART A). Start heating to allow melting of items 1 and 3
2. Heat ingredients in Part A to 80-85° C. while mixing gently until liquid and all of item 3 has melted and a homogeneous mixture is obtained. It is important that all of the paraffin (item 3) is melted. A clear, golden solution is obtained.
3. Gently cool to about 50-55° C., scraping the sides and bottom before adding PART B
4. In second double jacketed stainless steel tank add ingredients identified as 6-9 (PART B).
5. Mix items of Part B together until all of Cocamidopropyl PG-Dimonium Chloride Phosphate (item 8) has dissolved. Do not heat.
6. Add Part B to Part A while mixing and mix batch until homogeneous.
7. Slowly cool while mixing batch (preferably using sweep mixing) until room temperature. The formula will start thickening between 40-50° C. and solidify around 35° C.

EXAMPLE 2

Barrier Composition Comprising 0.8% Putrescine

The following barrier composition was prepared as described below.

TABLE 3

Barrier composition Formula A2 comprising 0.8% Putrescine.

| | Ingredients | CAS# | Grade | Amount (% W/W) |
|---|---|---|---|---|
| 1 | Petroleum Jelly (perfecta Petrolatum) | 8009-03-8 | USP | 45.50 |
| 2 | Mineral oil (white) | 8042-47-5 | USP | 34.00 |
| 3 | Paraffin (ceresin wax 130/135) | 8001-75-0 | MFR | 8.62 |
| 4 | Lanolin oil | 70321-63-0/ 8038-43-5 | MFR | 4.60 |
| 5 | Bisabolol | 23089-26-1 | USP | 0.48 |
| 6 | Putrescine (1, 4-diaminobutane) | 110-60-1 or 333-93-7 | MFR | 0.80 |
| 7 | Cocamidopropyl PG-Dimonium Chloride Phosphate | 83682-78-4 | MFR | 4.00 |
| 8 | Glycerin | 56-81-5 | USP | 1.00 |
| 9 | Panthenol (DL) | 16485-10-2 | MFR | 1.00 |
| | | | | 100% |

The above composition was prepared by adding and mixing the ingredients as described in Example 1 In a stainless steel tank equipped with a lightening-type propeller mixer.

EXAMPLE 3

Barrier Composition Comprising 0.8% Putrescine and 0.5%3-O-Ethyl Ascorbic Acid

The following barrier composition was prepared as described below.

TABLE 4

Barrier composition Formula B comprising 0.8% Putrescine and 0.5% 3-O-ethyl Ascorbic Acid.

| | Ingredients | CAS# | Grade | Amount (% W/W) |
|---|---|---|---|---|
| 1 | Petroleum Jelly (Perfecta Petrolatum) | 8009-03-8 | USP | 45.00 |
| 2 | White Mineral oil | 8042-47-5 | USP | 34.00 |
| 3 | Paraffin (ceresin wax 130/135) | 8001-75-0 | MFR | 8.60 |
| 4 | Lanolin oil | 70321-63-0/ 8038-43-5 | MFR | 4.60 |
| 5 | Bisabolol | 23089-26-1 | USP | 0.50 |

TABLE 4-continued

Barrier composition Formula B comprising 0.8% Putrescine and 0.5% 3-O-ethyl Ascorbic Acid.

| | Ingredients | CAS# | Grade | Amount (% W/W) |
|---|---|---|---|---|
| 6 | Cocamidopropyl PG-Dimonium Chloride Phosphate | 83682-78-4 | MFR | 4.00 |
| 7 | Putrescine (1, 4-diaminobutane | 110-60-1 or 333-93-7 | MFR | 0.80 |
| 8 | Glycerin | 56-81-5 | USP | 1.00 |
| 9 | Panthenol (DL) | 16485-10-2 | MFR | 1.00 |
| 10 | 3-O-Ethyl Ascorbic Acid (3-O-EAA, ET-VC ™) | 86404-04-8 | MFR | 0.50 |
| | | | | 100% |

The above composition was prepared by adding and mixing the ingredients as follows:

TABLE 5

Manufacturing procedure of Formula B.

Step# Manufacturing Procedure

1. In a double jacketed stainless steel tank equipped with a lightening type propeller add ingredients identified as 1 to 5 (PART A).
2. Heat ingredients to 80-85° C. while mixing gently until liquid and all of item 3 has melted and a homogeneous mixture is obtained.
3. In second double jacketed stainless steel tank add ingredients identified as 6-10 in the order listed (PART B).
4. Mix items of Part B one item at a time, mix until items 6, 7, 8, 9 & 10 have dissolved well and a white frothy lather is obtained.
5. At 50-55 degrees Celsius, add Part B to Part A while mixing and mix batch until homogeneous.
6. Slowly cool while mixing batch to desired consistency.

EXAMPLE 4

Barrier Composition Comprising 0.4% Putrescine and 0.5%3-O-Ethyl Ascorbic Acid

The following barrier composition was prepared as described below.

TABLE 6

Barrier composition Formula C comprising 0.4% Putrescine and 0.5% 3-O-ethyl Ascorbic Acid.

| | Ingredients | CAS# | Grade | Amount (% W/W) |
|---|---|---|---|---|
| 1 | Petroleum Jelly (Perfecta Petrolatum) | 8009-03-8 | USP | 46.20 |
| 2 | White Mineral oil | 8042-47-5 | USP | 34.90 |
| 3 | Paraffin (ceresin wax 130/135) | 8001-75-0 | MFR | 8.8.00 |
| 4 | Lanolin oil | 70321-63-0/ 8038-43-5 | MFR | 4.70 |
| 5 | Bisabolol | 23089-26-1 | USP | 0.50 |
| 6 | Cocamidopropyl PG-Dimonium Chloride Phosphate | 83682-78-4 | MFR | 2.00 |
| 7 | Putrescine (1, 4-diaminobutane | 110-60-1 or 333-93-7 | MFR | 0.40 |
| 8 | Glycerin | 56-81-5 | USP | 1.00 |
| 9 | Panthenol (DL) | 16485-10-2 | MFR | 1.00 |
| 10 | 3-O-Ethyl Ascorbic Acid (3-O-EAA, ET-VC ™) | 86404-04-8 | MFR | 0.5 |
| | | | | 100% |

The above composition was prepared as described in Example 3.

EXAMPLE 5

Barrier Composition Comprising 0.8% Putrescine and 0.5% Ascorbyl Palmitate

The following barrier composition was prepared as described below.

TABLE 7

Barrier composition Formula D comprising 0.8% Putrescine and 0.5% Ascorbyl Palmitate.

| | Ingredients | CAS# | Grade | Amount (% W/W) |
|---|---|---|---|---|
| 1 | Petroleum Jelly | 8009-03-8 | USP | 45.00 |
| 2 | Mineral oil (white) | 8042-47-5 | USP | 34.00 |
| 3 | Paraffin (ceresin wax) | 8001-75-0 | MFR | 8.62 |
| 4 | Lanolin oil | 70321-63-0/ 8038-43-5 | MFR | 4.60 |
| 5 | Bisabolol | 23089-26-1 | USP | 0.48 |
| 6 | Putrescine (1, 4-diaminobutane) | 110-60-1 or 333-93-7 | MFR | 0.80 |
| 7 | Glycerin | 56-81-5 | USP | 1.00 |
| 8 | Cocamidopropyl PG-Dimonium Chloride Phosphate (Cola Lipid C) | 83682-78-4 | MFR | 4.00 |
| 9 | Panthenol | 16485-10-2 | MFR | 1.00 |
| 10 | Ascorbyl palmitate | 137-66-6 | MFR | 0.5 |
| | | | | 100% |

Another composition lacking Ascorbyl palmitate was also prepared. In such case, the absence of Ascorbyl palmitate was compensated by Petroleum Jelly.

The above composition was prepared by adding and mixing the ingredients as follows in a stainless steel tank equipped with a lightening-type propeller mixer.

TABLE 8

Manufacturing procedure of Formula D.

| Step | Manufacturing Procedure |
|---|---|
| 1 | Add ingredients of items 1-5 in a first stainless steel tank (Part A) |
| 2 | Heat ingredients to 80-85° C. while mixing gently until liquid and all of item 3 has melted and a homogenous mixture is obtained. |
| 3 | In a second double jacketed stainless steel tank add ingredients listed under items 6-10 (Part B). |
| 4 | Mix items 6-10 together until putrescine and panthenol have dissolved. |
| 5 | At 50-55° C., add Part B to Part A with mixing and mix batch until homogeneous. |
| 6 | Slowly cool while mixing batch until room temperature. |

EXAMPLE 6

Effect of the Barrier Composition Comprising 0.8% Putrescine

A clinical study was performed on 10 subjects having undergone laser treatment for mole removal. Subjects applied a thin layer of the composition of Example 2 twice a day (morning and night) on the treated area for 12 weeks. Application of the composition decreased healing time as compared to untreated subjects having undergone the same type of laser treatment.

EXAMPLE 7

Stability of Compositions of the Present Invention

Preliminary stability tests of compositions of the present invention comprising putrescine (from 0.4% or 0.8%) and optionally 0.5% Vitamin C (Ascorbyl palmitate or 3-O-Ethyl Ascorbic Acid) show that the compositions are stable. Indeed, no significant change in color, odor and texture (including absence of multiple phases, and precipitate) were observed after about 12 months. Further stability tests are underway and are conducted as follows.

TABLE 9

Stability program design for putrescine barrier formulations.
Stability Program Design
25° C. /~2 to 75% RH

| Time Points (months) | 0 | 3 | 6 | 9 | 12 | 18 | 24 | 30 | 36 | 42 | 48 |
|---|---|---|---|---|---|---|---|---|---|---|---|
| 1) Organoleptic | C | C | C* | C | C* | C | C* | C | C* | C | C* |
| 2) Viscosity: USP <912>: [1] | | | | | | | | | | | |
| 3) Assay Vitamin C: HPLC Method[2] | | | | | | | | | | | |
| 4) Assays Putrescine: HPLC Method[3] | | | | | | | | | | | |

C = Anticipated results must be conform to all testing specifications
C* = only time point 0, 6, 12, 24, 36 & 48 will be tested for viscosity since not enough samples
[1] The Viscosity must be similar to the initial one over time ±10% (Just on the slow release formula: Barrier composition Formula A2 comprising 0.8% Putrescine.)
[2] The Vitamin C must be ±10% of the initial concentration of the formula, if present
[3] The Putrescine must be ±10% of the initial concentration of the formula
Quantity of unit needed:
Viscosity: 300 mL min: 15 tubes of 30 mL
Essays: 1 g: 1 tube of 30 mL
Total: 16 tubes Preliminary Stability Results Compositions comprising Ascorbyl Palmitate, were much less stable than compositions comprising 3-O-ethyl Ascorbic Acid, when combined with putrescine. Indeed, formula comprising Ascorbyl Palmitate changed color (turned to brown) much more rapidly than compositions comprising 3-O-ethyl Ascorbic Acid in combination with putrescine in the ointment base.

Results obtained thus far from ongoing stability assays for formula A1, A2, B and C are provided in Tables 10-13 below.

TABLE 10

Formula A1 (Example 1).

Finished Product Testing Specification — RD-12-00

| Test | Specification | Method or Reference | Initial Testing | RD-12-00 3 Mth | RD-12-00 6 Mth | RD-12-00 9 Mth |
|---|---|---|---|---|---|---|
| Appearance | Beige to pale yellow | Organoleptic | Pale yellow | Beige to pale yellow gel | Yellow gel | Pale yellow gel |
| 1,4-Diaminobutane Dihydrochloride (%) concentration | Target: 0.4% | QIN-10-205 | 0.4 | 0.3 | 0.4 | 0.4 |

TABLE 11

Formula A2 (Example 2).

Finished Product Testing Specification — SK-38-00 SK-38-00 SK-38-00

| Test | Specification | Method or Reference | Initial Testing | 3 Mth | 6 Mth |
|---|---|---|---|---|---|
| Appearance | Beige to pale yellow*gel) (*Product becomes pale yellow with time) | Organoleptic | Pale yellow gel | Beige gel | Pale yellow gel |
| Viscosity variation cP | | USP <912> | 212 400 | NT | 243 600 |
| 1, 4-Diaminobutane Dihydrochloride (%) concentration | Target: 0.8% | QIN-10-205 | 0.7 | 0.9 | 0.7 |

TABLE 12

Formula B (Example 3).

Finished Product Testing Specification — RD-13-00

| Test | Specification | Method or Reference | Initial Testing | RD-13-00 3 Mth | RD-13-00 6 Mth | RD-13-00 9 Mth |
|---|---|---|---|---|---|---|
| Appearance | Beige to pale yellow | Organoleptic | Pale yellow gel | Beige to pale yellow gel | Yellow gel | Pale yellow gel |
| 1,4-Diaminobutane Dihydrochloride (%) concentration | Target: 0.8% | QIN-10-205 | 0.9 | 0.7 | 0.8 | 0.7 |
| 3-O Ethyl Ascorbic Acid (%) concentration | Target: 0.5% | QIN-10-145 | 0.5 | 0.4 | 0.3 | 0.1 |

TABLE 13

Formula C (Example 4).

Finished Product Testing Specification — RD-13-00

| Test | Specification | Method or Reference | Initial Testing | RD-13-00 3 Mth | RD-13-00 6 Mth | RD-13-00 9 Mth |
|---|---|---|---|---|---|---|
| Appearance | Beige to pale yellow | Organoleptic | Pale yellow gel | Beige to pale yellow gel | Yellow gel | Pale yellow gel |
| 1,4-Diaminobutane Dihydrochloride (%) concentration | Target: 0.4% | QIN-10-205 | 0.5 | 0.3 | 0.4 | 0.4 |
| 3-O Ethyl Ascorbic Acid (%) concentration | Target: 0.5% | QIN-10-145 | 0.4 | 0.4 | 0.1 | 0.2 |

REFERENCES

1. Tajima S, Pinnell S R, Ascorbic acid preferentially enhances type I and III collagen transcription in human skin fibroblasts. J. Derm Science. 11:250-53, 1996. 2 Traikovich S S.
2. Use of topical ascorbic acid and its effects on photo damaged skin topography. Arch Otolaryngol Head Neck Surg 125:1091-98, 1999.
3. Murray J, Darr D, Reich J. Pinnell S. Topical vitamin C treatment reduces ultraviolet B radiation-included erythema in human skin. J. Invest Dermatol 1991:96:587 (abstract).
4. C. W. Lynde. Moisturizers: What they are and how they work. Skin Therapy Letter, 2001; http://www.skintherapyletter.com/2001/6.13/2.html

The invention claimed is:

1. A topical water free barrier composition comprising: (i) a primary aliphatic lower-alkyl (C1-5) polyamine in a concentration of between about 0.1% w/w to about 1% w/w; (ii) a phospholipid to encapsulate the primary polyamine, the phospholipid being cocamidopropyl PG-dimonium chloride phosphate in a concentration of between about 3% w/w and about 6% w/w; (iii) petroleum jelly in a concentration of between about 25% w/w and 65% w/w; and (iv) mineral oil in a concentration of between about 30% w/w and about 45% w/w.

2. The barrier composition of claim 1, wherein the polyamine is putrescine or dansylcadaverine.

3. The barrier composition of claim 1, wherein the polyamine is putrescine.

4. The barrier composition of claim 3, wherein the putrescine is in a concentration of between about 0.4% w/w and about 0.8% w/w.

5. The barrier composition of claim 1, wherein the petroleum jelly is in a concentration of about 45% w/w.

6. The barrier composition of claim 1, wherein the mineral oil is in a concentration of about 35% w/w.

7. The barrier composition of claim 1, wherein the cocamidopropyl PG-dimonium chloride phosphate is in a concentration of about 4% w/w.

8. The barrier composition of claim 1, further comprising (i) paraffin; (ii) lanolin oil; (iii) a lipophilic Vitamin C derivative; (iv) one or more humectants; and/or (v) bisabolol.

9. The barrier composition of claim 8, wherein the paraffin is in a concentration of between about 3% w/w and 15% w/w.

10. The barrier composition of claim 8, wherein the lanolin oil is in a concentration of between about 3% w/w and 6% w/w.

11. The barrier composition of claim 8, wherein the lipophilic Vitamin C derivative is in a concentration of between about 0.1% w/w and 10% w/w.

12. The barrier composition of claim 8, wherein the lipophilic Vitamin C derivative comprises 3-O-Ethyl Ascorbic Acid (3-O-EAA).

13. The barrier composition of claim 12, wherein the 3-O-EAA is in a concentration of about 0.5% w/w.

14. The barrier composition of claim 8, wherein the one or more humectants is(are) in a concentration of between about 0.5% w/w and 3% w/w.

15. The barrier composition of claim 8, wherein the one or more humectants comprise(s) glycerin, vitamin B5 or a combination thereof.

16. The barrier composition of claim 15, wherein the one or more humectants comprise(s) about 1% w/w of the glycerin and about 1% w/w of the Vitamin B5.

17. The barrier composition of claim 8, wherein the bisabolol is in a concentration of between about 0.1% w/w and 1% w/w.

18. A method of using the barrier composition defined in claim 1, for (i) treating of skin inflammation, treating skin irritation and/or reducing skin's signs of aging; (ii) promoting wound healing; or (iii) reducing formation of hypertrophic scar tissue, comprising topically administering the barrier composition on a subject.

* * * * *